(12) United States Patent
Haffner et al.

(10) Patent No.: US 7,488,303 B1
(45) Date of Patent: *Feb. 10, 2009

(54) OCULAR IMPLANT WITH ANCHOR AND MULTIPLE OPENINGS

(75) Inventors: David S. Haffner, Mission Viejo, CA (US); Gregory T. Smedley, Aliso Viejo, CA (US); Thomas W. Burns, Dana Point, CA (US); Hosheng Tu, Newport Coast, CA (US)

(73) Assignee: Glaukos Corporation, Laguna Hills, CA (US)

( * ) Notice: Subject to any disclaimer, the term of this patent is extended or adjusted under 35 U.S.C. 154(b) by 216 days.

This patent is subject to a terminal disclaimer.

(21) Appl. No.: 10/667,580

(22) Filed: Sep. 22, 2003

Related U.S. Application Data

(60) Provisional application No. 60/412,637, filed on Sep. 21, 2002.

(51) Int. Cl.
*A61M 5/00* (2006.01)
*A61M 25/00* (2006.01)
(52) U.S. Cl. .......................... 604/8; 604/521
(58) Field of Classification Search ............... 604/7–10, 604/264, 284, 521; 606/107, 108; 623/4.1
See application file for complete search history.

(56) References Cited

U.S. PATENT DOCUMENTS

| | | |
|---|---|---|
| 3,788,327 A | 1/1974 | Donowitz et al. |
| 4,037,604 A | 7/1977 | Newkirk |
| 4,168,697 A | 9/1979 | Cantekin |
| 4,175,563 A | 11/1979 | Arenberg et al. |
| 4,402,681 A | 9/1983 | Haas et al. |
| 4,428,746 A | 1/1984 | Mendez |

(Continued)

FOREIGN PATENT DOCUMENTS

AU 200072059 A1 12/2000

(Continued)

OTHER PUBLICATIONS

Troncoso, Manuel U., Tanatlum Implants for inducing hypotony, American Journal of Opthalmology, vol. 32, No. 4, Apr. 1949, pp. 499-508 (11 pages).

(Continued)

*Primary Examiner*—Leslie R Deak
(74) *Attorney, Agent, or Firm*—Knobbe Martens Olson & Bear, LLP

(57) ABSTRACT

An implant for treating an ocular disorder has a longitudinal implant axis, an outflow portion passing therethrough, a plurality of longitudinally spaced openings therein, an inflow portion, and an anchoring member that extends from the implant and is disposed distally of the openings. The outflow portion is shaped and sized to be introduced into Schlemm's canal of an eye at an angle, and received at least partially within Schlemm's canal regardless of its rotational orientation about the axis during introduction. The openings allow fluid communication from a lumen within the outflow portion to a location outside the outflow portion. The inflow portion is configured to be positioned within an anterior chamber of the eye to permit fluid communication from the anterior chamber to the outflow portion. The axis extends through a trabecular meshwork of the eye and is generally orthogonal to Schlemm's canal during the fluid communication.

14 Claims, 12 Drawing Sheets

U.S. PATENT DOCUMENTS

| | | | |
|---|---|---|---|
| 4,501,274 A | 2/1985 | Skjaerpe | |
| 4,521,210 A | 6/1985 | Wong | |
| 4,554,918 A | 11/1985 | White | |
| 4,604,087 A | 8/1986 | Joseph | |
| 4,632,842 A | 12/1986 | Karwoski et al. | |
| 4,634,418 A | 1/1987 | Binder | |
| 4,718,907 A | 1/1988 | Karwoski et al. | |
| 4,722,724 A | 2/1988 | Schocket | |
| 4,733,665 A | 3/1988 | Palmaz | |
| 4,750,901 A | 6/1988 | Molteno | |
| 4,787,885 A * | 11/1988 | Binder | 604/8 |
| 4,804,382 A | 2/1989 | Turina et al. | |
| 4,820,626 A | 4/1989 | Williams et al. | |
| 4,846,172 A | 7/1989 | Berlin | |
| 4,863,457 A | 9/1989 | Lee | |
| 4,886,488 A | 12/1989 | White | |
| 4,900,300 A | 2/1990 | Lee | |
| 4,936,825 A | 6/1990 | Ungerleider | |
| 4,946,436 A | 8/1990 | Smith | |
| 4,968,296 A | 11/1990 | Ritch et al. | |
| 5,041,081 A | 8/1991 | Odrich | |
| 5,073,163 A | 12/1991 | Lippman | |
| 5,092,837 A | 3/1992 | Ritch et al. | |
| 5,095,887 A | 3/1992 | Leon et al. | |
| 5,127,901 A | 7/1992 | Odrich | |
| 5,129,895 A | 7/1992 | Vassiliadis et al. | |
| 5,171,213 A | 12/1992 | Price, Jr. | |
| 5,178,604 A | 1/1993 | Baerveldt et al. | |
| 5,180,362 A | 1/1993 | Worst | |
| 5,246,451 A | 9/1993 | Trescony et al. | |
| 5,290,295 A | 3/1994 | Querals et al. | |
| 5,300,020 A * | 4/1994 | L'Esperance, Jr. | 604/9 |
| 5,318,513 A | 6/1994 | Leib et al. | |
| 5,334,137 A | 8/1994 | Freeman | |
| 5,338,291 A | 8/1994 | Speckman et al. | |
| 5,346,464 A | 9/1994 | Camras | |
| 5,360,399 A | 11/1994 | Stegmann | |
| 5,370,607 A | 12/1994 | Memmen | |
| 5,370,641 A | 12/1994 | O'Donnell, Jr. | |
| 5,372,577 A | 12/1994 | Ungerleider | |
| 5,397,300 A | 3/1995 | Baerveldt et al. | |
| 5,433,701 A | 7/1995 | Rubinstein | |
| 5,454,796 A | 10/1995 | Krupin | |
| 5,472,440 A | 12/1995 | Beckman | |
| 5,476,445 A | 12/1995 | Baerveldt et al. | |
| 5,486,165 A | 1/1996 | Stegmann | |
| 5,516,522 A | 5/1996 | Peyman et al. | |
| 5,520,631 A | 5/1996 | Nordquist et al. | |
| 5,557,453 A | 9/1996 | Schalz et al. | |
| 5,558,629 A | 9/1996 | Baerveldt et al. | |
| 5,558,630 A | 9/1996 | Fisher | |
| 5,562,641 A | 10/1996 | Flomenblit et al. | |
| RE35,390 E | 12/1996 | Smith | |
| 5,601,094 A | 2/1997 | Reiss | |
| 5,601,549 A | 2/1997 | Miyagi | |
| 5,626,558 A | 5/1997 | Suson | |
| 5,626,559 A | 5/1997 | Solomon | |
| 5,639,278 A | 6/1997 | Dereume et al. | |
| 5,651,783 A | 7/1997 | Reynard | |
| 5,665,114 A | 9/1997 | Weadock et al. | |
| 5,670,161 A | 9/1997 | Healy et al. | |
| 5,676,679 A | 10/1997 | Simon et al. | |
| 5,681,275 A | 10/1997 | Ahmed | |
| 5,702,414 A | 12/1997 | Richter et al. | |
| 5,702,419 A | 12/1997 | Berry et al. | |
| 5,704,907 A | 1/1998 | Nordquist et al. | |
| 5,713,844 A | 2/1998 | Peyman | |
| 5,723,005 A | 3/1998 | Herrick | |
| 5,741,333 A | 4/1998 | Frid | |
| 5,743,868 A | 4/1998 | Brown et al. | |
| 5,752,928 A | 5/1998 | De Roulhac et al. | |
| 5,766,243 A | 6/1998 | Christensen et al. | |
| 5,785,674 A | 7/1998 | Mateen | |
| 5,807,302 A | 9/1998 | Wandel | |
| 5,810,870 A | 9/1998 | Myers et al. | |
| 5,830,139 A | 11/1998 | Abreu | |
| 5,830,171 A | 11/1998 | Wallace | |
| 5,836,939 A | 11/1998 | Negus et al. | |
| 5,865,831 A | 2/1999 | Cozean et al. | |
| 5,868,697 A | 2/1999 | Richter et al. | |
| 5,879,319 A | 3/1999 | Pynson et al. | |
| 5,882,327 A | 3/1999 | Jacob | |
| 5,886,822 A | 3/1999 | Spitzer | |
| 5,893,837 A | 4/1999 | Eagles et al. | |
| 5,908,449 A | 6/1999 | Bruchman et al. | |
| 5,932,299 A | 8/1999 | Katoot | |
| 5,968,058 A | 10/1999 | Richter et al. | |
| 5,981,598 A | 11/1999 | Tatton | |
| 6,004,302 A | 12/1999 | Brierley | |
| 6,007,510 A | 12/1999 | Nigam | |
| 6,007,511 A | 12/1999 | Prywes | |
| 6,033,434 A | 3/2000 | Borghi | |
| 6,045,557 A | 4/2000 | White et al. | |
| 6,050,970 A | 4/2000 | Baerveldt | |
| 6,059,772 A | 5/2000 | Hsia et al. | |
| 6,059,812 A | 5/2000 | Clerc et al. | |
| 6,063,116 A | 5/2000 | Kelleher | |
| 6,063,396 A | 5/2000 | Kelleher | |
| 6,071,286 A | 6/2000 | Mawad | |
| 6,077,299 A | 6/2000 | Adelberg et al. | |
| 6,102,045 A | 8/2000 | Nordquist et al. | |
| 6,142,990 A | 11/2000 | Burk | |
| 6,165,210 A | 12/2000 | Lau et al. | |
| 6,168,575 B1 | 1/2001 | Soltanpour | |
| 6,174,305 B1 | 1/2001 | Mikus et al. | |
| 6,187,016 B1 | 2/2001 | Hedges et al. | |
| 6,193,656 B1 | 2/2001 | Jeffries et al. | |
| 6,197,056 B1 | 3/2001 | Schachar | |
| 6,203,513 B1 | 3/2001 | Yaron et al. | |
| 6,228,873 B1 | 5/2001 | Brandt et al. | |
| 6,231,597 B1 | 5/2001 | Deem et al. | |
| 6,241,721 B1 | 6/2001 | Cozean et al. | |
| 6,254,612 B1 | 7/2001 | Hieshima | |
| 6,266,182 B1 | 7/2001 | Morita | |
| 6,268,398 B1 | 7/2001 | Ghosh et al. | |
| 6,342,058 B1 | 1/2002 | Portney | |
| 6,375,642 B1 | 4/2002 | Grieshaber et al. | |
| 6,428,501 B1 | 8/2002 | Reynard | |
| 6,450,984 B1 | 9/2002 | Lynch et al. | |
| 6,464,724 B1 | 10/2002 | Lynch et al. | |
| 6,524,275 B1 | 2/2003 | Lynch et al. | |
| 6,533,768 B1 | 3/2003 | Hill | |
| 6,544,249 B1 * | 4/2003 | Yu et al. | 604/521 |
| 6,585,680 B2 | 7/2003 | Bugge | |
| 6,626,858 B2 * | 9/2003 | Lynch et al. | 604/8 |
| 6,629,981 B2 | 10/2003 | Bui et al. | |
| 6,638,239 B1 | 10/2003 | Bergheim et al. | |
| 6,666,841 B2 | 12/2003 | Gharib et al. | |
| 6,699,211 B2 | 3/2004 | Savage | |
| D490,152 S | 5/2004 | Myall et al. | |
| 6,736,791 B1 | 5/2004 | Tu et al. | |
| 6,780,164 B2 | 8/2004 | Bergheim et al. | |
| 2002/0013546 A1 | 1/2002 | Grieshaber et al. | |
| 2002/0133168 A1 | 9/2002 | Smedley et al. | |
| 2002/0143284 A1 | 10/2002 | Tu et al. | |
| 2002/0169130 A1 | 11/2002 | Tu et al. | |
| 2002/0188308 A1 | 12/2002 | Tu et al. | |
| 2003/0009124 A1 | 1/2003 | Lynch et al. | |
| 2003/0055372 A1 | 3/2003 | Lynch et al. | |
| 2003/0060752 A1 | 3/2003 | Bergheim et al. | |
| 2003/0069637 A1 | 4/2003 | Lynch et al. | |
| 2003/0088260 A1 | 5/2003 | Smedley et al. | |
| 2003/0097151 A1 | 5/2003 | Smedley et al. | |
| 2003/0120200 A1 | 6/2003 | Bergheim et al. | |

| | | | |
|---|---|---|---|
| 2003/0181848 | A1 | 9/2003 | Bergheim et al. |
| 2003/0187384 | A1 | 10/2003 | Bergheim et al. |
| 2003/0187385 | A1 | 10/2003 | Bergheim et al. |
| 2003/0220602 | A1 | 11/2003 | Lynch et al. |
| 2003/0220603 | A1 | 11/2003 | Lynch et al. |
| 2003/0229303 | A1 | 12/2003 | Haffner et al. |
| 2003/0236484 | A1 | 12/2003 | Lynch et al. |
| 2004/0024345 | A1 | 2/2004 | Gharib et al. |
| 2004/0050392 | A1 | 3/2004 | Tu et al. |
| 2004/0102729 | A1 | 5/2004 | Haffner et al. |
| 2004/0111050 | A1 | 6/2004 | Smedley et al. |
| 2004/0127843 | A1 | 7/2004 | Tu et al. |

FOREIGN PATENT DOCUMENTS

| | | |
|---|---|---|
| CA | 2244646 | 8/1998 |
| DE | 198 40 047 A1 | 3/2000 |
| EP | 0 858 788 A1 | 8/1998 |
| EP | 0 898 947 A2 | 3/1999 |
| EP | 1 114 627 A1 | 11/2000 |
| FR | 2 710 269 | 9/1993 |
| GB | 2 296 663 A | 7/1996 |
| JP | 11-123205 | 1/1999 |
| WO | WO 91/18568 | 12/1991 |
| WO | WO 94/13234 | 6/1992 |
| WO | WO 92/19294 | 11/1992 |
| WO | WO 94/21205 | 9/1994 |
| WO | WO 95/08310 | 3/1995 |
| WO | WO 98/30181 | 1/1998 |
| WO | EO 89/00869 | 2/1998 |
| WO | WO 98/35639 | 8/1998 |
| WO | WO 99/26567 | 6/1999 |
| WO | WO 99/30641 | 6/1999 |
| WO | WO 99/38470 | 8/1999 |
| WO | WO 00/13627 | 3/2000 |
| WO | WO 00/64389 | 4/2000 |
| WO | WO 00/64390 | 4/2000 |
| WO | WO 00/64391 | 4/2000 |
| WO | WO 00/64393 | 11/2000 |
| WO | WO 00/72788 | 12/2000 |
| WO | WO 01/50943 | 7/2001 |
| WO | WO 01/78631 | 10/2001 |
| WO | WO 01/78656 | 10/2001 |
| WO | WO 03/015659 | 2/2003 |
| WO | WO 03/073968 | 9/2003 |

OTHER PUBLICATIONS

PCT Publication—WO 01/50943, International Publication Date Jul. 19, 2001.
Datlev Spiegel, 7 Chirurgische Glaukomtherapie, pp. 79-88.
L. Jay Katz, M.D., A Call for Innovative Operations for Glaucoma, Arch Ophthalmology, Mar. 2000, vol. 118, pp. 412-413.
Anselm Kampik and Franz Grehn, Nutzen und Risiken augenärztilchen Therapie, Hauptreferate der XXXIII, Essener Fortbildung für Augenärzte, Dec. 1998. (English translated version enclosed Benefits and Risks of Ophthalmological Therapy.).
Phillip C. Jacobi, MD, Thomas S. Dietlein, MD, and Gunter K. Krieglstein, MD., Goniocurettage for Removing Trabecular Meshwork: Clinical Results of a New Surgical Technique in Advanced Cronic Open-Angle Glaucoma, American Journal of Ophthalmology, May 1999, pp. 505-510.
Phillip C. Jacobi, MD, Thomas S. Dietlein, MD, and Gunter K. Krieglstein, MD., Bimanual Trabecular Aspiration in Pseudoexfoliation Glaucoma, Ophthalmology, 1998, vol. 105, No. 5, May 1998, pp. 886-894.
Phillip C. Jacobi, MD, Thomas S. Dietlein, MD, and Gunter K. Krieglstein, MD., Microendoscopic Trabecular Surgery in Glaucoma Management, Ophthalmology, 1999, vol. 106, No. 3, pp. 538-544.

Arthue L. Schwartz, MD, and Douglas R. Anaderson, MD, Trabeculaar Surgery, Arch Ophthalmol, vol. 92, Aug. 1974, pp. 134-138.
R.A. Hill, Q, Ren, D.D. Nguyen, L-H Liaw, and M.W. Berns, Free-Electron Laser (FEL) Ablation of Ocular Tissues, Lasesr Med Sci 1998, pp. 13:219-226.
Maurice H. Luntz, MD, and D.G. Livingston, B.S.C., Trabeculotomy AB Externo and Trabeculectomy in Congenital and Adult-Onset Glaucoma, American Journal of Ophthalmology, Feb. 1977, vol. 83, No. 2, pp. 174-179.
W.M. Grant, MD, Further Studies on Facility of Flow Through the Trabecular Meshwork, A.M.A. Archives of Ophthalmology, Oct. 1958, vol. 60, pp. 523-533.
Richard A. Hill, MD, George Baerveldt, MD, Serdar A. Ozler, MD, Michael Pickford, BA, Glen A. Profeta, BS, and Michael W. Berns,PhD, Laser Trabecular Ablation (LTA), Laser in Surgery and Medicine, 1991, vol. 11, 99. 341-346.
Detlev Spiegel, MD, Karin Kobuch, MD, Richard A. Hill, MD, Ronald L. Gross, MD, Schlemm's Canal Implant: A new Method to Lower Intraocular Pressure in Patients With POAG, Ophthalmic Surgery and Lasers, Jun. 1999, vol. 30, No. 6, pp. 492-494.
Hans Hoerauf, Christopher Wibelauer, Christian Scholz, Ralf Engelhardt, Peter Koch, Horst Laqua, and Reginald Birngruber, Slit-Lamp-Adapted Optical Coherence Tomography of the Anterluor Segment, Graefe's Arch Clin. Exp. Ophthalmol, May, 1999, vol. 238, pp. 8-18.
Sumita Radhakrishnam, Andrew M. Rollins, Jonathan E. Roth, S. Yazddanfar, Volker Westphal, David Bardenstein, and Joseph Izatt, Real-Time Optical Coherence Tomography of the Anterior Segment at 1310 nm, Arch Ophthalmology, Aug. 2001, vol. 119, pp. 1179-1185.
I. Grierson, R.C. Howes, and Q. Wang, Age-related Changes in the Canal of Schlemm, Exp. Eye Res., 1985, vol. 39, pp. 505-512.
Luanna K. Putney, Cecite Rose T. Vibat, and Martha E. O'Donnell, Intracellular C1 Regulates Na-K-C1 Cotransport Activity in Human Trabecular Meshwork Cells, 1999 American Physiological Society, Sep. 1999, pp. C373 through C383.
Edited by Kevin Strange, Cellular and Molecular Physiology of Cell Volume Regulation, Library of Congress Cataloging in-Publication Data, CRC Press, Inc., pp. 312-321, 1983.
William Tatton, Ruth M.E. Chalmers-Redman, Ajay Sud, Steven M. Podos, and Thomas Mittag Mainataining Mitochondrial Membrane Impermeability: An Opportunity for New Therapy in Glaucoma, Survey of Ophthalmology, vol. 45, Supplement 3, May 2001, pp. S277 through S283.
Robert W. Nickells, Apoptosis of Retinal Ganglion Cells in Glaucoma: An Update of the Molecular Pathways Involved in Cell Death, Survey of Ophthalmology, vol. 43, Supplement 1, Jun. 1999, pp. S-151 through S-161.
Grune & Stratton, Harcourt Brace Jovanovich Publishers, edited by J.E. Caims, Glaucoma, vol. 1, Chapter 14, Anatomy of the Aqueous Outflow Channels, by Johannes W. Rohen, pp. 277-296, 1986.
Yasuhiro Matsumoto and Douglas H. Johnson, Trabecular Meshwork Phagocytosis in Graucomatous Eyes, Ophthalmologica 1977, vol. 211, pp. 147-152.
M. Bruce Shields, MD, A Study Guide for Glaucoma: Aqueous Humor Dynamics, Copyright 1982, pp. 6-43.
M.A. Johnstone, R. Stegmann, and B.A. Smit, American Glaucoma Society, 12th Annual Meeting, Cylindrical Tubular Structures Spanning from Trabecular Meshwork Across SC, Laboratory Studies with SEM, TEM and Tracers Correlated with Clinical Findings, p. 39, 2002.
W.G. Tatton, Apoptotic Mechanisms in Neurodegeneration: Possible Relevance to Glaucoma, European Journal of Ophthalmology, Jan.-Mar. 1999, vol. 9, Supplement 1, pp. S22 through S29.
U.S. Appl. No. 09/452,963, filed Dec. 2, 1999, entitled Expandable/Retractable Stent for Venous Valvular Annulus Use.

* cited by examiner

OCULAR IMPLANT WITH ANCHOR AND MULTIPLE OPENINGS

CROSS-REFERENCE TO RELATED APPLICATION

This application claims the priority benefit of U.S. Provisional Application No. 60/412,637, filed Sep. 21, 2002, the entirety of which is hereby incorporated by reference.

FIELD OF THE INVENTION

The present invention generally relates to improved medical devices and methods for the reduction of elevated pressure in organs of the human body. More particularly, the present invention relates to the treatment of glaucoma by implanting a glaucoma stent in an eye to reduce the intraocular pressure, wherein the glaucoma stent is to drain aqueous from the anterior chamber by bypassing diseased trabecular meshwork at the level of trabecular meshwork and use/restore existing outflow pathways.

BACKGROUND OF THE INVENTION

About two percent of people in the United States have glaucoma. Glaucoma is a group of eye diseases that causes pathological changes in the optic disk and corresponding visual field loss resulting in blindness if untreated. Intraocular pressure elevation is the major etiologic factor in all glaucomas.

In glaucomas associated with an elevation in eye pressure the source of resistance to outflow is in the trabecular meshwork. The tissue of the trabecular meshwork allows the "aqueous" to enter Schlemm's canal, which then empties into aqueous collector channels in the posterior wall of Schlemm's canal and then into aqueous veins. The aqueous or aqueous humor is a transparent liquid that fills the region between the cornea at the front of the eye and the lens. The aqueous humor is constantly secreted by the ciliary body around the lens, so there is a continuous flow of the aqueous humor from the ciliary body to the eye's front chamber. The eye's pressure is determined by a balance between the production of aqueous and its exit through the trabecular meshwork (major route) or via uveal scleral outflow (minor route). The trabecular meshwork is located between the outer rim of the iris and the internal periphery of the cornea. The portion of the trabecular meshwork adjacent to Schlemm's canal causes most of the resistance to aqueous outflow (juxtacanilicular meshwork).

Glaucoma is grossly classified into two categories: closed-angle glaucoma and open-angle glaucoma. The closed-angle glaucoma is caused by closure of the anterior angle by contact between the iris and the inner surface of the trabecular meshwork. Closure of this anatomical angle prevents normal drainage of aqueous humor from the anterior chamber of the eye. Open-angle glaucoma is any glaucoma in which the angle of the anterior chamber remains open, but the exit of aqueous through the trabecular meshwork is diminished. The exact cause for diminished filtration is unknown for most cases of open-angle glaucoma. However, there are secondary open-angle glaucomas that may include edema or swelling of the trabecular spaces (from steroid use), abnormal pigment dispersion, or diseases such as hyperthyroidism that produce vascular congestion.

All current therapies for glaucoma are directed at decreasing intraocular pressure. This is initially by medical therapy with drops or pills that reduce the production of aqueous humor or increase the outflow of aqueous. However, these various drug therapies for glaucoma are sometimes associated with significant side effects, such as headache, blurred vision, allergic reactions, death from cardiopulmonary complications and potential interactions with other drugs. When the drug therapy fails, surgical therapy is used. Surgical therapy for open-angle glaucoma consists of laser (trabeculoplasty), trabeculectomy and aqueous shunting implants after failure of trabeculectomy or if trabeculectomy is unlikely to succeed. Trabeculectomy is a major surgery that is most widely used and is augmented with topically applied anticancer drugs such as 5-flurouracil or mitomycin-c to decrease scarring and increase surgical success.

Approximately 100,000 trabeculectomies are performed on Medicare age patients per year in the United States. This number would increase if the morbidity associated with trabeculectomy could be decreased. The current morbidity associated with trabeculectomy consists of failure (10-15%), infection (a life long risk about 2-5%), choroidal hemorrhage (1%, a severe internal hemorrhage from pressure too low resulting in visual loss), cataract formation, and hypotony maculopathy (potentially reversible visual loss from pressure too low).

If it were possible to bypass the local resistance to outflow of aqueous at the point of the resistance and use existing outflow mechanisms, surgical morbidity would greatly decrease. The reason for this is that the episcleral aqueous veins have a backpressure that would prevent the eye pressure from going too low. This would virtually eliminate the risk of hypotony maculopathy and choroidal hemorrhage. Furthermore, visual recovery would be very rapid and risk of infection would be very small (a reduction from 2-5% to 0.05%). Because of these reasons surgeons have tried for decades to develop a workable surgery for the trabecular meshwork.

The previous techniques, which have been tried, are goniotomy/trabeculotomy, and other mechanical disruption of the trabecular meshwork, such as trabeculopuncture, goniophotoablation, laser trabecular ablation and goniocurretage. They are briefly described below.

Goniotomy/Trabeculotomy: Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed secondary to repair mechanisms and a process of "filling in". The filling in is the result of a healing process that has the detrimental effect of collapsing and closing in of the created opening throughout the trabecular meshwork. Once the created openings close, the pressure builds back up and the surgery fails.

Trabeculopuncture: Q-switched Neodymium (Nd):YAG lasers also have been investigated as an optically invasive technique for creating full-thickness holes in trabecular meshwork. However, the relatively small hole created by this trabeculopuncture technique exhibits a filling in effect and fails.

Goniophotoablation/Laser Trabecular Ablation: Goniophotoablation is disclosed by Berlin in U.S. Pat. No. 4,846,172, and describes the use of an excimer laser to treat glaucoma by ablating the trabecular meshwork. This was not demonstrated by clinical trial to succeed. Hill et al. used an Erbium:YAG laser to create full thickness holes through trabecular meshwork (Hill et al., Lasers in Surgery and Medicine 11:341-346, 1991). This technique was investigated in a primate model and a limited human clinical trial at the University of California, Irvine. Although morbidity was zero in both trials, success rates did not warrant further human trials. Failure again was from filling in of created defects in trabecular meshwork by repair mechanisms. Neither of these is a valid surgical technique for the treatment of glaucoma.

Goniocurretage: This is an ab-interno (from the inside) mechanical disruptive technique. This uses an instrument similar to a cyclodialysis spatula with a microcurrette at the tip. Initial results are similar to trabeculotomy that fails secondary to repair mechanisms and a process of filling in.

Although trabeculectomy is the most commonly performed filtering surgery, Viscocanulostomy (VC) and non-penetrating trabeculectomy (NPT) are two new variations of filtering surgery. These are ab-externo (from the outside), major ocular procedures in which Schlemm's canal is surgically exposed by making a large and very deep scleral flap. In the VC procedure, Schlemm's canal is cannulated and viscoelastic substance injected (which dilates Schlemm's canal and the aqueous collector channels). In the NPT procedure, the inner wall of Schlemm's canal is stripped off after surgically exposing the canal.

Trabeculectomy, VC, and NPT are performed under a conjunctival and scleral flap, such that the aqueous humor is drained onto the surface of the eye or into the tissues located within the lateral wall of the eye. Normal physiological outflows are not used. These surgical operations are major procedures with significant ocular morbidity. When Trabeculectomy, VC, and NPT are thought to have a low chance for success, a number of implantable drainage devices have been used to ensure that the desired filtration and outflow of aqueous humor through the surgical opening will continue. The risk of placing a glaucoma drainage implant also includes hemorrhage, infection and postoperative double vision that is a complication unique to drainage implants.

All of the above embodiments and variations thereof have numerous disadvantages and moderate success rates. They involve substantial trauma to the eye and require great surgical skill by creating a hole over the full thickness of the sclera/cornea into the subconjunctival space. Furthermore, normal physiological outflow pathways are not used. The procedures are mostly performed in an operating room generating a facility fee, anesthesiologist's professional fee and have a prolonged recovery time for vision. The complications of filtration surgery have inspired ophthalmic surgeons to look at other approaches to lowering intraocular pressure.

The trabecular meshwork and juxtacanilicular tissue together provide the majority of resistance to the outflow of aqueous and, as such, are logical targets for surgical removal in the treatment of open-angle glaucoma. In addition, minimal amounts of tissue are altered and existing physiologic outflow pathways are utilized. Trabecular bypass surgery has the potential for much lower risks of choroidal hemorrhage, infection and uses existing physiologic outflow mechanisms. This surgery could be performed under topical anesthesia in a physician's office with rapid visual recovery.

Therefore, there is a great clinical need for the treatment of glaucoma by a method that would be faster, safer and less expensive than currently available modalities. Trabecular bypass surgery is an innovative surgery that uses a micro stent, shunt, or other implant to bypass diseased trabecular meshwork alone at the level of trabecular meshwork and use or restore existing outflow pathways. The object of the present invention is to provide a means and methods for treating elevated intraocular pressure in a manner which is simple, effective, disease site specific and can be performed on an outpatient basis.

SUMMARY OF THE INVENTION

Some aspects of the invention comprise an implant for treating glaucoma, the implant comprising: a first portion configured to be embedded in the sclera of an eye, to anchor the implant; a second portion configured to be positioned in the anterior chamber of the eye and to receive fluid from the anterior chamber; an intermediate portion between the first portion and the second portion, the intermediate portion configured to span the trabecular meshwork of the eye, so as to permit drainage of fluid between the anterior chamber and Schlemm's canal; and a plurality of longitudinally spaced openings in the intermediate portion.

Some aspects of the invention comprise an implant for treating glaucoma in an eye, the implant having a longitudinal implant axis, and comprising: an outflow portion through which the longitudinal implant axis passes, the outflow portion shaped and sized to be: (a) introduced through Schlemm's canal of the eye with the portion of the longitudinal implant axis at an angle to Schlemm's canal; and (b) received at least partially within Schlemm's canal regardless of a rotational orientation of the outflow portion about the longitudinal implant axis during the introduction; a plurality of openings in the outflow portion, the openings allowing fluid to communicate from a lumen within the outflow portion to a location outside the outflow portion; an inflow portion configured to permit communication of fluid from the anterior chamber of the eye to the outflow portion; and an anchoring member at one end of the implant.

Some aspects of the invention comprise an implant for treating glaucoma, comprising: an outflow portion, sized and shaped to be received at least partially within Schlemm's canal; an inflow portion in fluid communication with the outflow portion, the inflow portion configured to be disposed in the anterior chamber of the eye; and a central portion extending between the inflow and outflow portions; the outflow portion having a diameter that is no more than three times the diameter of the central portion; a plurality of openings in the outflow portion, the openings allowing fluid to communicate from a lumen within the outflow portion to a location outside the outflow portion; and an anchoring member at one end of the implant, the anchoring member configured to anchor the implant in the sclera of the eye.

In some embodiments, the implant further comprises at least one opening in the central portion.

Some aspects of the invention comprise a kit for delivering implants for treating an ophthalmic condition, the kit comprising: an elongate body, the elongate body sized to be introduced into an eye through an incision in the eye; an implant positionable on or in the elongate body, the implant comprising: an outflow portion, sized and shaped to be received at least partially within Schlemm's canal; an inflow portion in fluid communication with the outflow portion, the inflow portion configured to be disposed in the anterior chamber of the eye; a plurality of openings in the outflow portion, the openings allowing fluid to communicate from a lumen within the outflow portion to a location outside the outflow portion; and an anchoring member at one end of the implant, the anchoring member configured to anchor the implant in the sclera of the eye.

In some embodiments, the elongate body in the kit comprises a tube, and the implant is positionable at least partially in the tube.

Some embodiments comprise method of treating glaucoma, the method comprising: inserting an elongate body into the trabecular meshwork and Schlemm's canal of an eye, the elongate body comprising a plurality of fluid channels and a plurality of openings, each of the openings permitting fluid to flow from at least one of the channels through the opening to a location outside the elongate body; and introducing fluid through at least two of the fluid channels into the eye.

Some embodiments further comprise positioning the implant such that a first opening of said plurality of openings is at Schlemm's canal of the eye. Some embodiments further comprise positioning the implant such that a second opening of said plurality of openings is at the trabecular meshwork and/or the sclera of the eye.

In some embodiments, the inserting comprises inserting the elongate body from the anterior chamber through the trabecular meshwork of the eye and into Schlemm's canal of the eye.

Some embodiments include implanting a trabecular stent in an eye to reduce intraocular pressure, wherein the trabecular stent drains aqueous from the anterior chamber by bypassing diseased trabecular meshwork at the level of trabecular meshwork and use existing outflow pathways.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF THE PREFERRED EMBODIMENT

Figure 1:
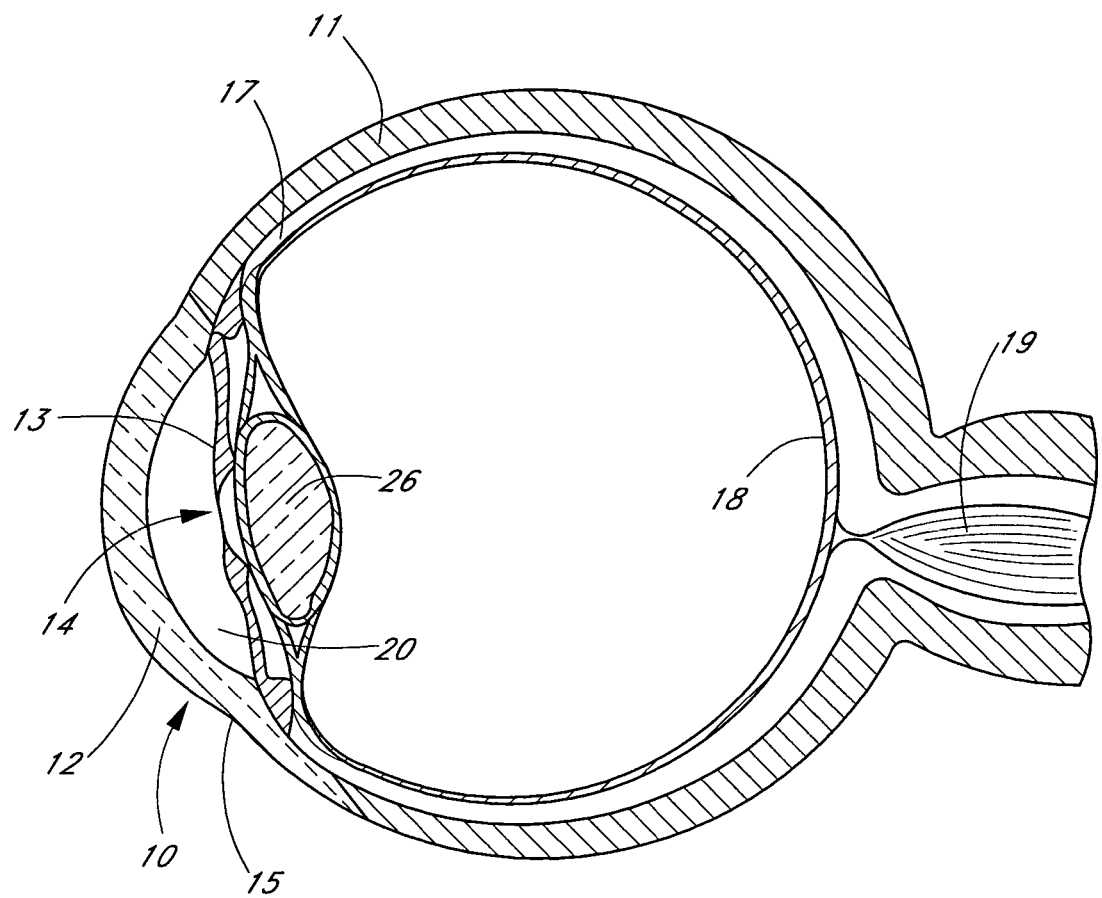
FIG. 1 is a sectional view of an eye.

In accordance with a preferred method, trabecular bypass surgery creates an opening or a hole through the diseased trabecular meshwork through minor microsurgery. To prevent "filling in" of the hole, a biocompatible elongate implant is placed within the hole as a trabecular stent, which may include, for example, a solid rod or hollow tube. In one exemplary embodiment, the trabecular stent implant may be positioned across the diseased trabecular meshwork alone and it does not extend into the eye wall or sclera. In another embodiment, the inlet end of the implant is exposed to the anterior chamber of the eye while the outlet end is positioned at the exterior surface of the trabecular meshwork. In another exemplary embodiment, the outlet end is positioned at and over the exterior surface of the trabecular meshwork and into the fluid collection channels of the existing outflow pathways. In still another embodiment, the outlet end is positioned in the Schlemm's canal. In an alternative embodiment, the outlet end enters into fluid collection channels up to the level of the aqueous veins with the trabecular stent inserted in a retrograde or antegrade fashion.

According to some embodiments, the trabecular stent implant is made of biocompatible material, which is either hollow to allow the flow of aqueous humor or solid biocompatible material that imbibes aqueous. The material for the trabecular stent may be selected from the group consisting of porous material, semi-rigid material, soft material, hydrophilic material, hydrophobic material, hydrogel, elastic material, and the like.

In further accordance with some embodiments, the trabecular stent implant may be rigid or it may be made of relatively soft material and is somewhat curved at its distal section to fit into the existing physiological outflow pathways, such as Schlemm's canal. The distal section inside the outflow pathways may have an oval shape to stabilize the trabecular stent in place without undue suturing. Stabilization or retention of the trabecular stent may be further strengthened by a taper end and/or by at least one ridge or rib on the exterior surface of the distal section of the trabecular stent, or other surface alterations designed to retain the trabecular stent.

In one embodiment, the trabecular stent may include a micropump, pressure sensor, one-way valve, or semi-permeable membrane to minimize reflux of red blood cells or serum protein. It may also be useful to use a biocompatible material that hydrates and expands after implantation so that the trabecular stent is locked into position around the trabecular meshwork opening or around the distal section of the trabecular stent.

One of the advantages of trabecular bypass surgery, as disclosed herein, and the use of a trabecular stent implant to bypass diseased trabecular meshwork at the level of trabecular meshwork and thereby use existing outflow pathways is that the treatment of glaucoma is substantially simpler than in existing therapies. A further advantage of the invention is the utilization of simple microsurgery that may be performed on an outpatient basis with rapid visual recovery and greatly decreased morbidity. Finally, a distinctly different approach is used than is found in existing implants. Physiological outflow mechanisms are used or re-established by the implant of the present invention, in contradistinction with previously disclosed methodologies. The procedure for implanting a trabecular stent of the present invention may be accomplished by ab interno and/or ab externo procedures.

FIGS. 1 to 7 show an embodiment of a glaucoma stent and its delivery system for the treatment of glaucoma by implanting a trabecular or glaucoma stent. In particular, a trabecular stent implant is used to bypass diseased trabecular meshwork at the level of trabecular meshwork to use or restore existing outflow pathways and methods thereof.

Figure 2:
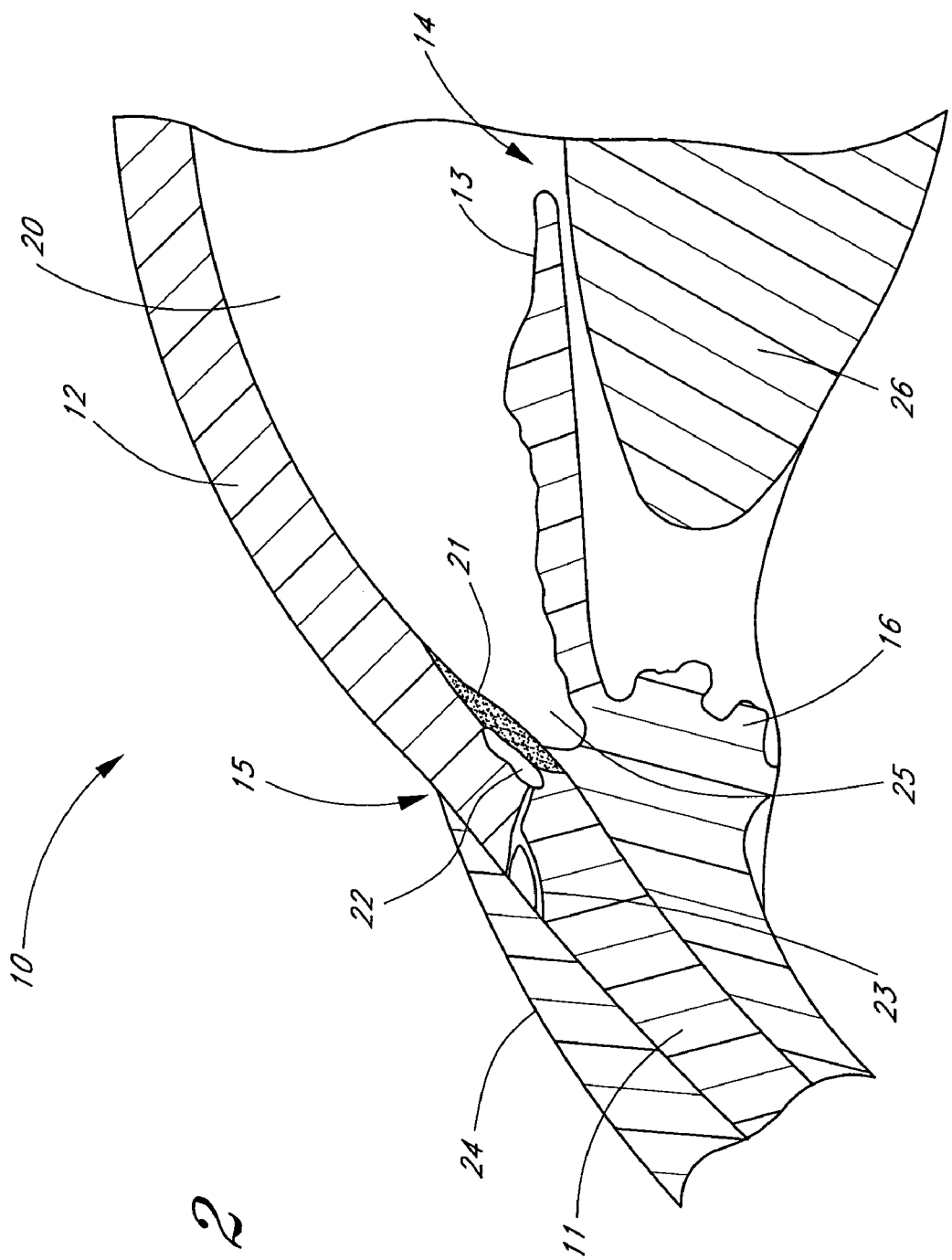
FIG. 2 is a close-up sectional view, showing the anatomy of the trabecular meshwork and the anterior chamber of the eye.

For background illustration, FIG. 1 shows a sectional view of an eye 10, while FIG. 2 shows a close-up view, showing the relative anatomical locations of the trabecular meshwork, the anterior chamber, and Schlemm's canal. Thick collagenous tissue known as sclera 11 covers the entire eye 10 except that portion covered by the cornea 12. The cornea 12 is a thin transparent tissue that focuses and transmits light into the eye and the pupil 14, which is the circular hole in the center of the iris 13 (colored portion of the eye). The cornea 12 merges into the sclera 11 at a juncture referred to as the limbus 15. The ciliary body 16 begins internally in the eye and extends along the interior of the sclera 11 and becomes the choroid 17. The choroid 17 is a vascular layer of the eye underlying retina 18. The optic nerve 19 transmits visual information to the brain and is sequentially destroyed by glaucoma.

The anterior chamber 20 of the eye 10, which is bound anteriorly by the cornea 12 and posteriorly by the iris 13 and lens 26, is filled with aqueous. Aqueous is produced primarily by the ciliary body 16 and reaches the anterior chamber angle 25 formed between the iris 13 and the cornea 12 through the pupil 14. In a normal eye, the aqueous is removed through the trabecular meshwork 21. Aqueous passes through trabecular meshwork 21 into Schlemm's canal 22 and through the aqueous veins 23, which merge with blood-carrying veins, and into venous circulation. Intraocular pressure of the eye 10 is maintained by the intricate balance of secretion and outflow of the aqueous in the manner described above. Glaucoma is characterized by the excessive buildup of aqueous fluid in the anterior chamber 20, which produces an increase in intraocular pressure (fluids are relatively incompressible and pressure is directed equally to all areas of the eye).

As shown in FIG. 2, the trabecular meshwork 21 constitutes a small portion of the sclera 11. It is understandable that creating a hole or opening for implanting a device through the tissues of the conjunctiva 24 and sclera 11 is relatively a major surgery as compared to a surgery for implanting a device through the trabecular meshwork 21 only.

Some embodiments include a method for increasing aqueous humor outflow in an eye of a patient to reduce the intraocular pressure therein. The method comprises bypassing diseased trabecular meshwork at a level of the trabecular meshwork with a trabecular stent implant and using existing outflow pathways. The trabecular stent implant may be an elongate trabecular stent or other appropriate shape, size, or configuration. In one embodiment of an elongate trabecular stent implant, the trabecular stent has an inlet end, an outlet end and a lumen therebetween, wherein the inlet end is positioned at an anterior chamber of the eye and the outlet end is positioned at about an exterior surface of the diseased trabecular meshwork. Furthermore, the outlet end may be positioned into fluid collection channels of the existing outflow pathways. Optionally, the existing outflow pathways may comprise Schlemm's canal 22. The outlet end may be further positioned into fluid collection channels up to the level of the aqueous veins with the trabecular stent inserted either in a retrograde or antegrade fashion with respect to the existing outflow pathways.

In a further alternate embodiment, a method is disclosed for increasing aqueous humor outflow in an eye of a patient to reduce an intraocular pressure therein. The method comprises (a) creating an opening in trabecular meshwork, wherein the trabecular meshwork comprises an interior side and exterior side; (b) inserting a trabecular stent implant into the opening; and (c) transporting the aqueous humor by the trabecular stent implant to bypass the trabecular meshwork at the level of the trabecular meshwork from the interior side to the exterior side of the trabecular meshwork.

The trabecular stent implant may comprise a biocompatible material, such as a medical grade silicone, for example, the material sold under the trademark Silastic™, which is available from Dow Corning Corporation of Midland, Mich., or polyurethane, which is sold under the trademark Pellethane™, which is also available from Dow Corning Corporation. In an alternate embodiment, other biocompatible materials (biomaterials) may be used, such as polyvinyl alcohol, polyvinyl pyrolidone, collagen, heparinized collagen, tetrafluoroethylene, fluorinated polymer, fluorinated elastomer, flexible fused silica, polyolefin, polyester, titanium, stainless steel, Nitinol, shape-memory material, polysilicon, mixture of biocompatible materials, and the like. In a further alternate embodiment, a composite biocompatible material by surface coating the above-mentioned biomaterial may be used, wherein the coating material may be selected from the group consisting of polytetrafluoroethylene (PTFE), polyimide, hydrogel, heparin, therapeutic drugs, and the like.

Figure 3:
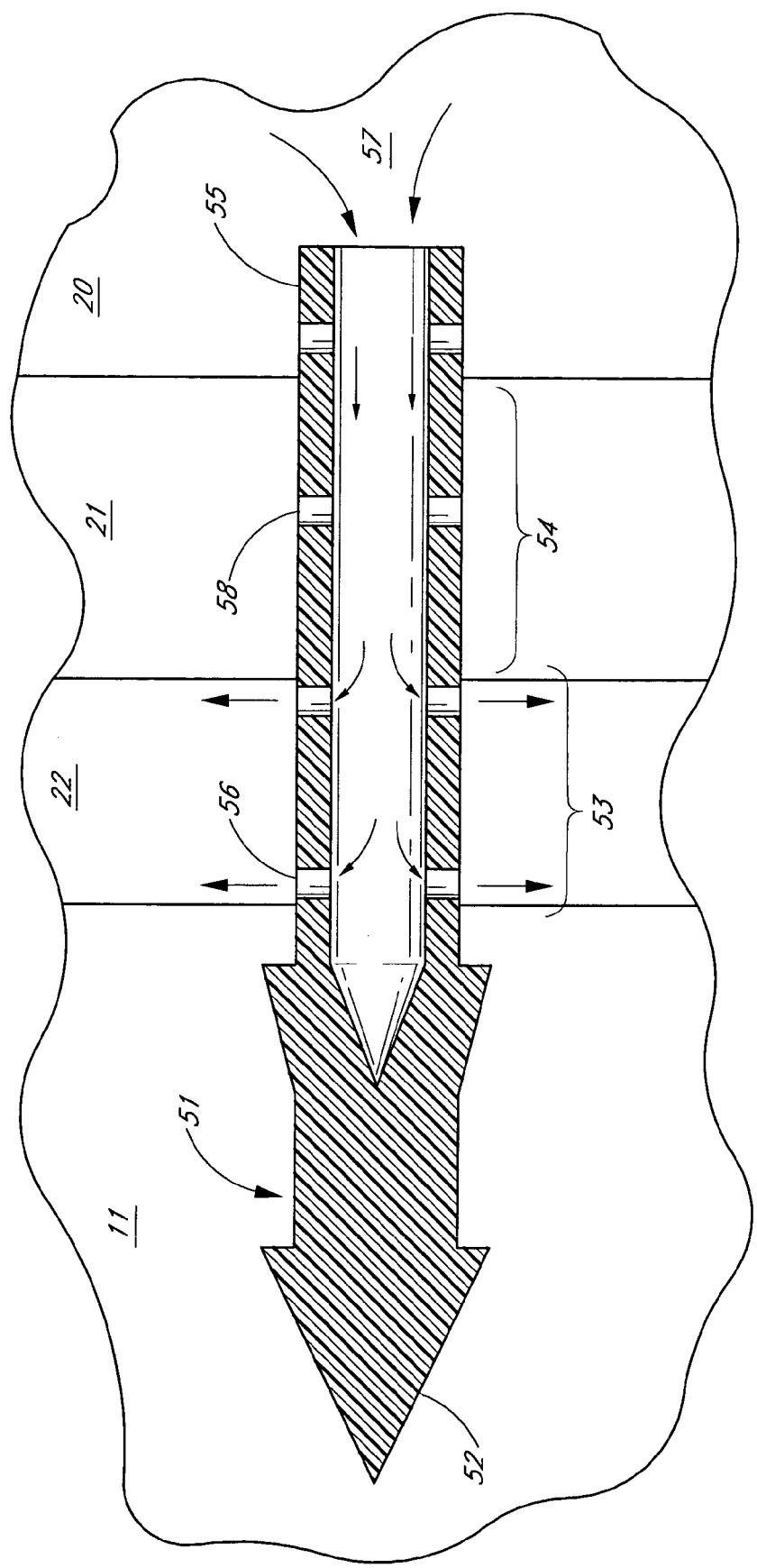
FIG. 3 is an axisymmetric glaucoma stent that is intended to be placed noncircumferentially in Schlemm's canal.

FIG. 3 shows an axisymmetric glaucoma stent that is intended to be placed non-circumferentially in Schlemm's canal 22 (i.e., with its long axis at an angle relative to the circumference of Schlemm's canal 22), and that transports aqueous 57 from the anterior chamber 20 to Schlemm's canal. The stent may comprises a trephining head 52 at the distal end of the stent 51, wherein the trephining head 52 is sized and configured to penetrate the trabecular meshwork 21, Schlemm's canal 22 into sclera 11 for anchoring. The outlet portion 53 may comprise a plurality of outlet openings 56 spaced apart axially and configured for releasing aqueous into Schlemm's canal 22 with ease. The middle section 54 of the stent is generally placed at about the trabecular meshwork 21, wherein the middle section may optionally comprise a plurality of openings 58 spaced apart for effectively releasing aqueous 57 into trabecular meshwork. The proximal end 55 of the stent 51 is generally disposed in the anterior chamber 20 at a location not to affect the aqueous flow or eye tissue movement. An axisymmetric stent of the present invention is to overcome the flow resistance in Schlemm's canal when a conventional stent is placed circumferentially along the Schlemm's canal passageway that tends to direct the aqueous flow in a defined direction.

Figure 4:
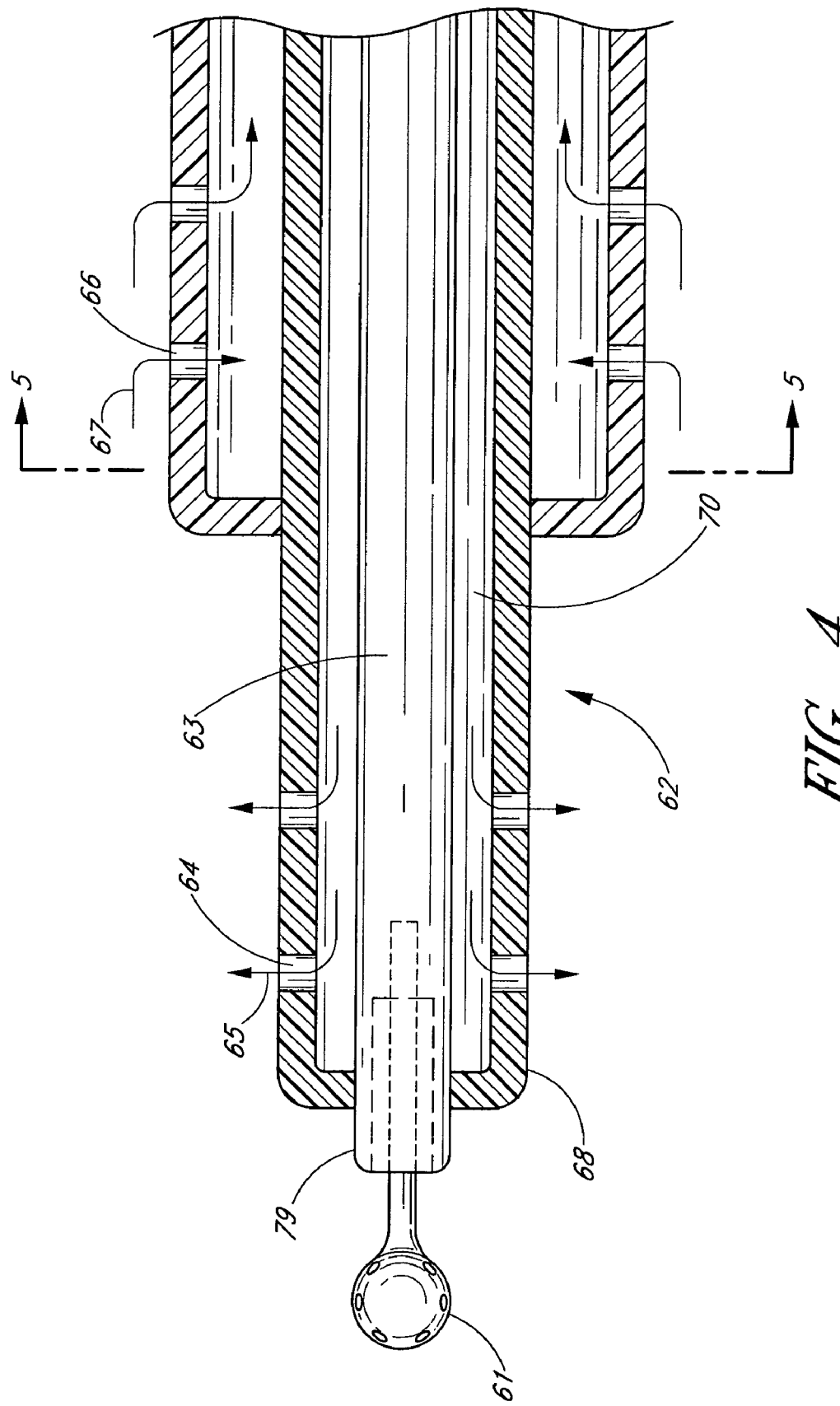
FIG. 4 is a stent delivery system comprising irrigation and aspiration capabilities.

FIG. 4 shows a stent delivery system 62 comprising irrigation 64 and aspiration 67 capabilities. A trabecular or glaucoma stent 61, particularly an axisymmetric stent, is placed and grasped by a grasping tip 79 at the distal section of a delivery system 62. In one aspect, the grasping tip 79 in a stent delivery system with irrigation/aspiration is accomplished with a concentric tubing 68 having swaged end details. The irrigation step 64 is carried out by injecting fluid out of the irrigation ports 65 to the anterior chamber 20. The aspiration step 67 is carried out by returning fluid entering the aspiration ports 66. A plunger or releasing element 63 is located concentrically within the lumen 70 of the delivery system 62. In one embodiment, after the stent is placed in the target location, the tubing 68 is withdrawn back toward the handpiece (at right-hand side in FIG. 4; not shown) to release the stent 61.

Figure 5:
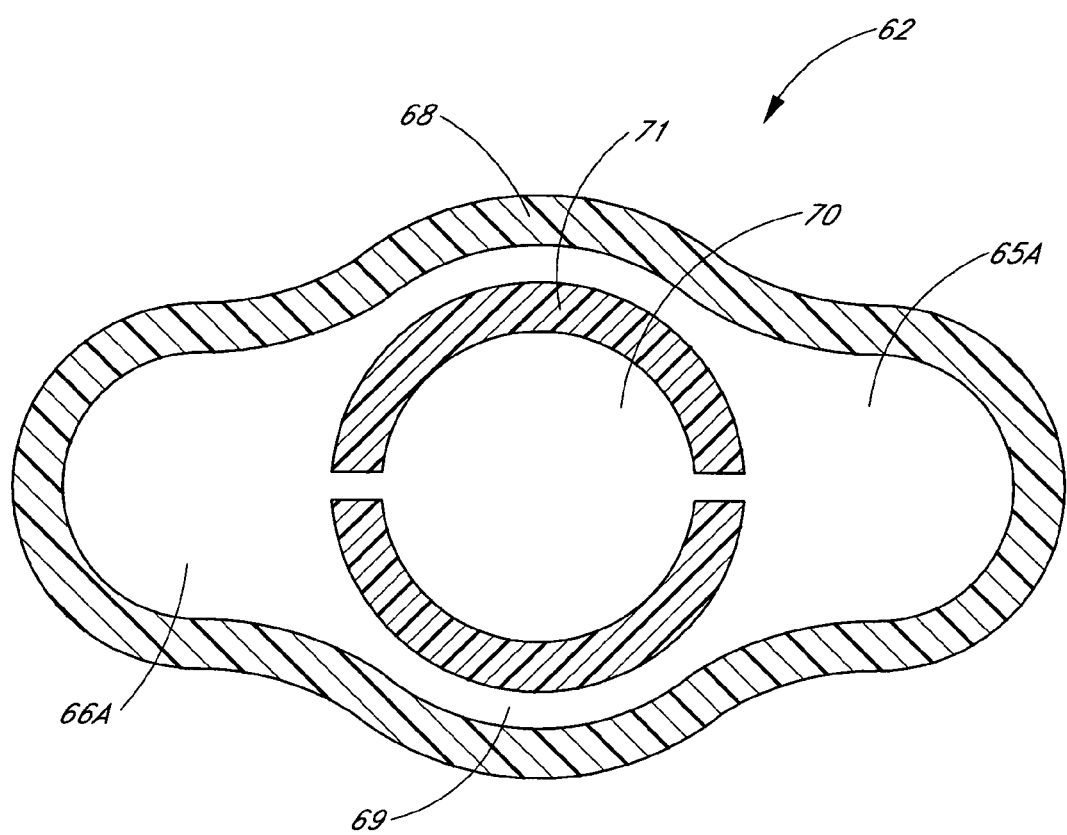
FIG. 5 is a cross-sectional view of the stent delivery system of FIG. 4.

FIG. 5 shows cross-sectional view of the stent delivery system 62 of FIG. 4. The tubing 68 of the stent delivery system may be formed on mandrel to create a first side channel 65A for irrigation and a second side channel 66A for aspiration. The tight fit 69 between an inner tubing 71 and the outer tubing 68 creates barrier between the channel 65A for irrigation and the channel 66A for aspiration.

Figure 6:
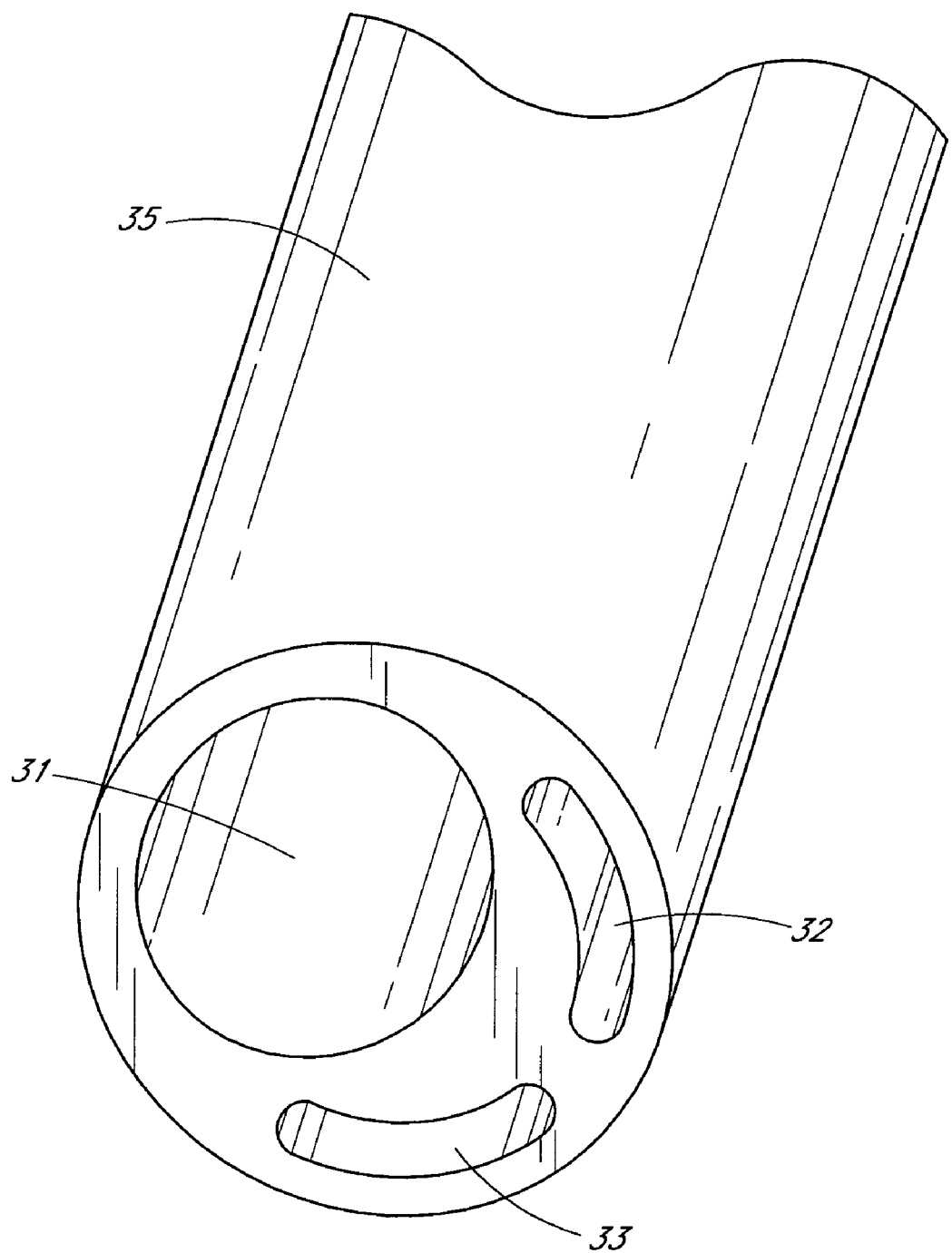
FIG. 6 is a multi-lumen tubing shaft as a component of the stent delivery system.

FIG. 6 shows a multi-lumen tubing shaft 35 as a component of the stent delivery system 62. This is an alternate configuration for fluid irrigation and aspiration. The tubing shaft 35 comprises a central lumen 31 that may carry a grasping tip 79 for stent folding. The auxiliary lumens 32, 33 spaced apart or spaced at an opposite side of the central lumen 31 are provided for fluid irrigation/aspiration.

Figure 7:
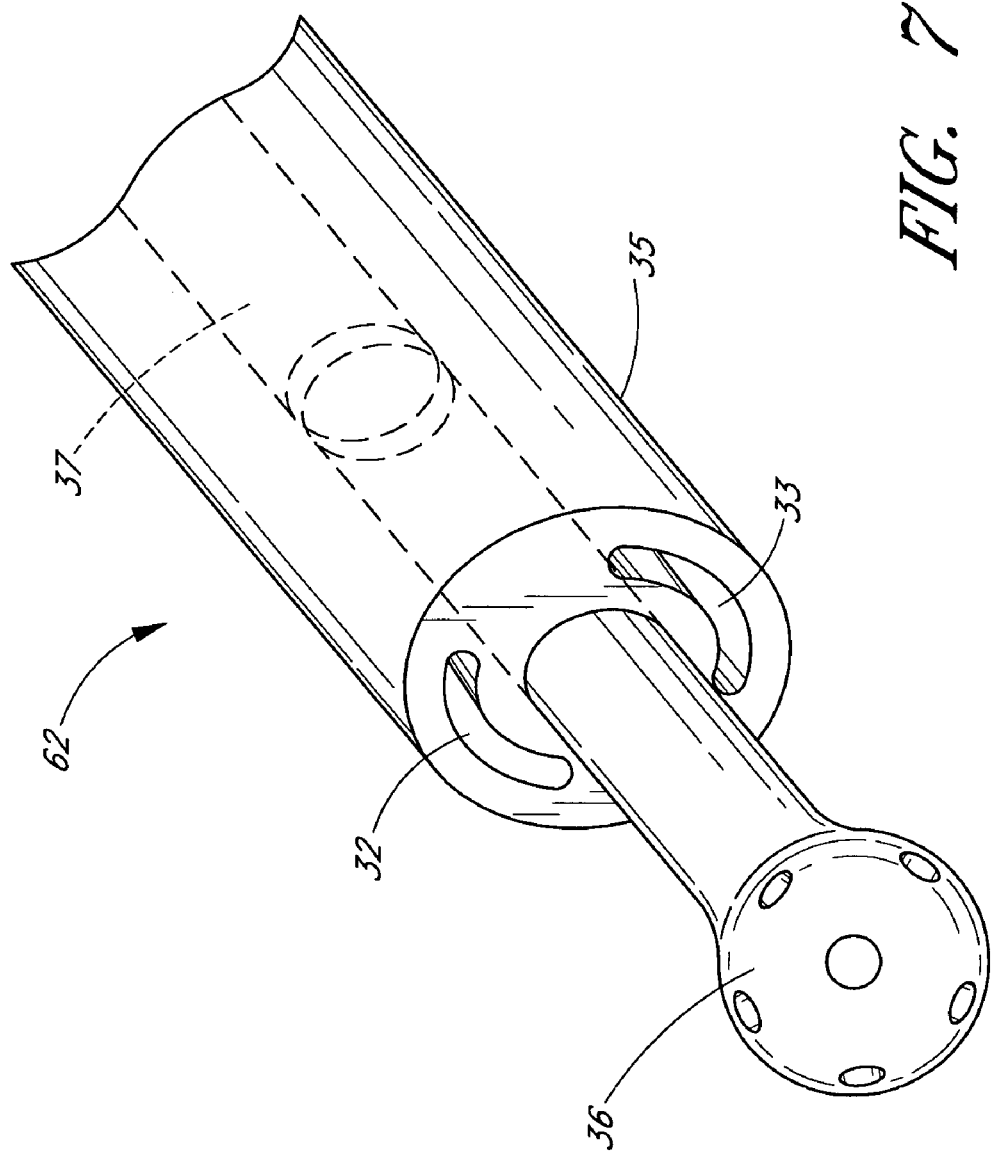
FIG. 7 is a perspective view of the stent with a stent delivery system.

FIG. 7 shows a perspective view of the stent with a stent delivery system. In an alternate embodiment, the delivery system 62 may comprise a stainless cone pin 37. The pin 37 is fixed relatively to the stent 36, preferably an axisymmetric stent, when the stent is placed at a target location, say inside Schlemm's canal or at least a portion of the stent exposing to Schlemm's canal or to a collecting channel. Instead of pushing the pin 37 forward to release the stent 36, it is configured to pull back the multi-lumen tubing 35 so as to release the stent out of the grasping tip 79.

In another aspect, the delivery system may comprise a retainer ring on the tubing 35, wherein the retainer ring is attached to a triggering mechanism in the handle and is used to pull back the outer sleeve (or the tubing 35) with an economical construction or manufacturing method.

Other aspects of the present invention may comprise sending irrigation fluid, including viscoelastic, down the center a stent delivery system. It is further disclosed that light means may be sent down a clear pathway or through a clear extrusion for better visualization, using the extrusion itself for light transmission. It is another object of the present disclosure to provide fiber optic imaging to validate placement of a stent in the target location, say Schlemm's canal. In another aspect, it is provided to using collet style mechanism to grip or grasp a stent during a delivery phase or to retrieve objects in the cavity of a body. It is also a common practice to use footswitch to release a stent in the body.

Some aspects of the invention relate to a trabecular stent comprising a distal end, a proximal end, and a plurality of outlet openings spaced apart axially, wherein the proximal end is placed in an anterior chamber and the distal end is placed in a sclera posterior to Schlemm's canal, at least one opening being exposed to Schlemm's canal.

In still another aspect of the present disclosure, RF energy or other suitable energy (thermal, cryo, or laser) is used to release a stent from its grasping tip. In a previously disclosed bifurcatable stent, the stent may be sized and configured to have at least one retaining arm at the end section of the stent body that is about perpendicular to the stent body, wherein a first retaining arm is used to be placed inside Schlemm's canal.

Figure 8:
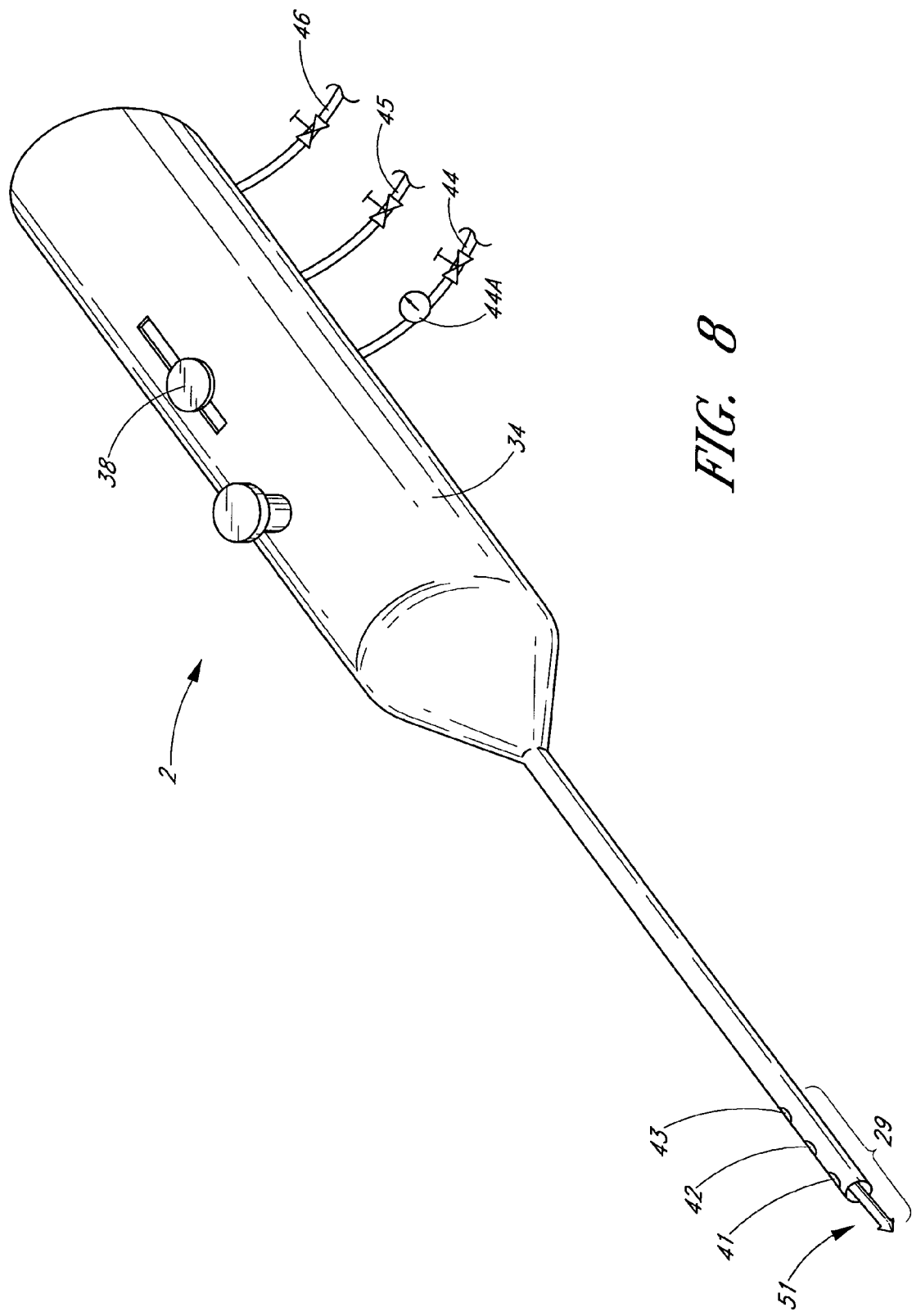
FIG. 8 is one embodiment of an ab interno stent delivery applicator.

FIG. 8 shows one embodiment of an ab interno stent delivery applicator 2. The applicator 2 comprises a distal section 29 and a handle section 34. A stent 51 is loaded at the distal section 29 of the applicator. The applicator further comprises a plurality of fluid ports 41, 42, 43 for administering various fluids to various target tissue sites. For example, the first fluid port 41 is connected through a fluid channel 47 to a fluid supplier source 44, wherein the fluid port 41 is configured to be placed at about the sclera 11 of an eye 10 during the stent delivery phase. At least one component of the fluid exiting the first fluid port 41 is selected from a group consisting of genes, growth factors, drugs, or nutrients for treating the sclera. In another example, the second fluid port 42 is connected through a fluid channel 48 to a fluid supplier source 45, wherein the fluid port 42 is configured to be placed at about Schlemm's canal 22 of an eye 10 during the stent delivery phase. At least one component in the fluid exiting the second fluid port 42 is selected from a group consisting of vasodilating agent, anti-glaucoma drug, and other drug suitably for treating Schlemm's canal. In still another example, the third fluid port 43 is connected through a fluid channel 49 to a fluid supplier source 46, wherein the fluid port 43 is configured to be placed at about the trabecular meshwork 21 of an eye 10 during the stent delivery phase. At least one component in the fluid exiting the third fluid port 43 may comprise, but not limited to, vasodilating agent, anti-glaucoma drug, balanced saline solution or viscoelastic for treating trabecular meshwork. All fluid channels 47, 48, and 49 of the applicator are suitably placed within a lumen 7 of the stent delivery applicator 2.

Figure 9:
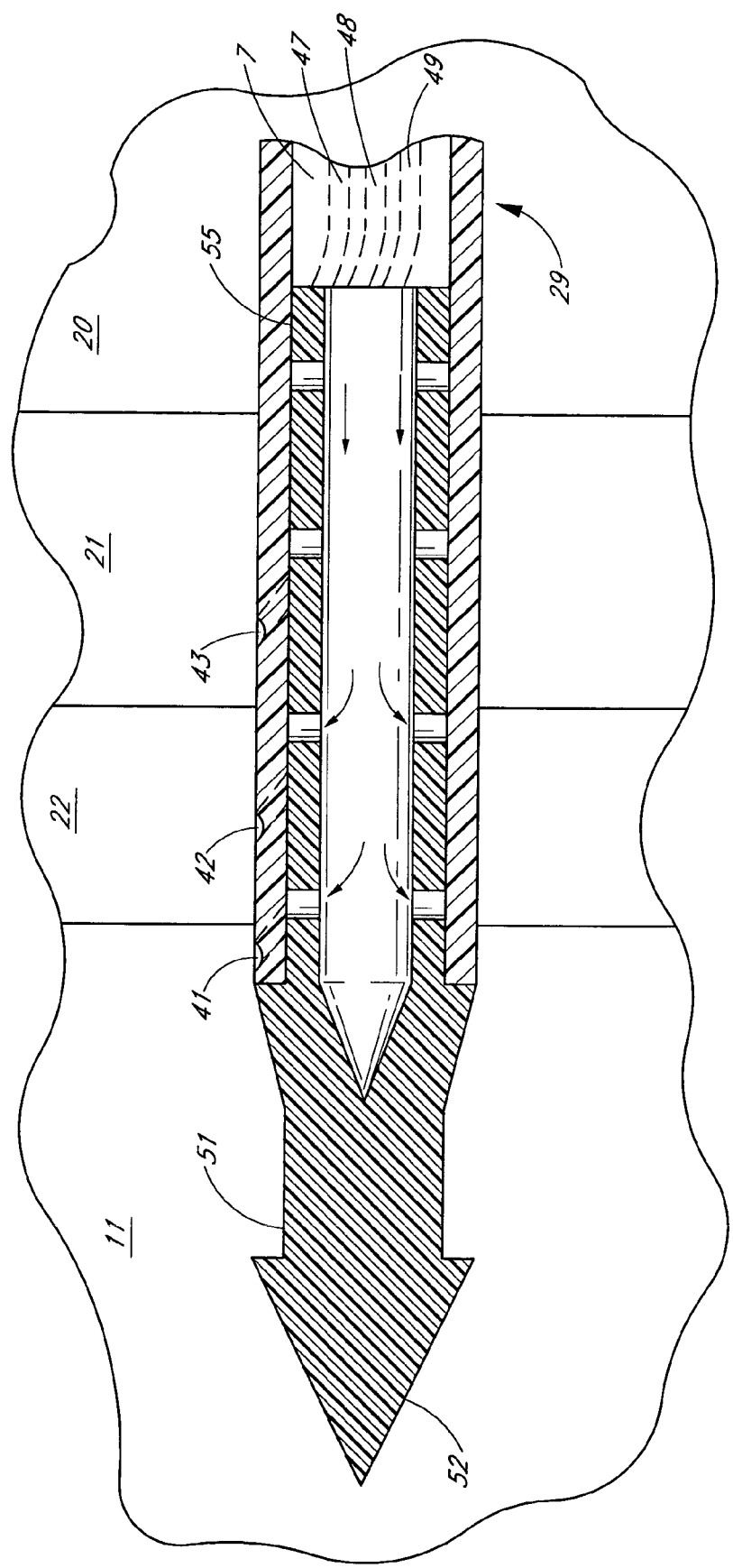
FIG. 9 shows a distal section of the ab interno stent delivery applicator of FIG. 8.

FIG. 9 shows a distal section 29 of the ab interno stent delivery applicator 2 of FIG. 8. In one embodiment, a pressure monitor 44A is installed at a suitable place adjacent to the fluid supplier source 44, wherein the pressure monitor 44A is sized and configured to monitor the sensing pressure at about the first fluid port 41. During the course of the stent delivery phase, the sensing pressure at the first fluid port 41 reflects the pressures of the anterior chamber 20, the trabecular meshwork 21, Schlemm's canal 22, and the sclera 11 in sequence. In one embodiment, when the sensing pressure measured suddenly increases due to flow resistance from the sclera, it is indicative that the distal end of the stent 51 is well in place in the sclera. Appropriate fluid can be administered to the sclera 11 through the first fluid port 41. Similarly, a second appropriate fluid can be administered to Schlemm's canal through the second fluid port 42. And a third appropriate fluid can be administered to trabecular meshwork through the third fluid port 43. At the end of the stent delivery phase, the stent 51 can be unloaded from the applicator 2 by operating a knob 38 on the handle 34. Also shown are fluid channels 47, 48, and 49 of the applicator within the lumen 7 of the stent delivery applicator 2.

Figure 10:
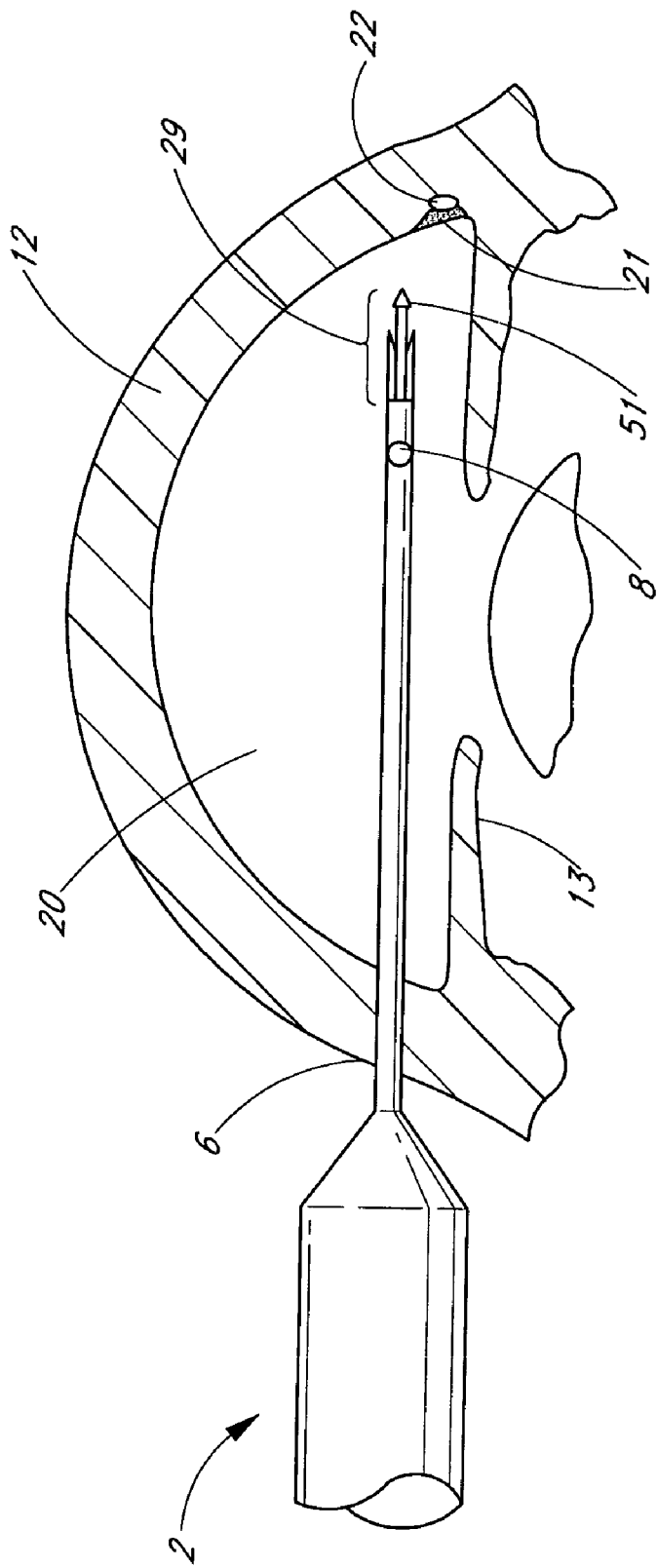
FIG. 10 shows a procedure for implanting a stent in an ab interno process.

FIG. 10 shows a procedure for implanting a stent 51 in an ab interno process. First, a small incision 6 is created at an appropriate location of the cornea 12 allowing inserting an applicator 2 into the anterior chamber. The distal section 29 of the applicator 2 advances across the eye and approaches the trabecular meshwork 21. By further advancing the distal end, the distal section 29 of the applicator 2 passes trabecular meshwork, Schlemm's canal and reaches the sclera 11 behind Schlemm's canal for anchoring the distal end of the stent into the sclera. The stent is unloaded from the applicator thereafter.

Some aspects of the invention relate to a stent delivery apparatus comprising a plurality of fluid exiting ports configured axially along a distal section of the apparatus, wherein each port is connected to a fluid supply, at least one fluid exiting port is exposed to a sclera to provide a fluid to the sclera. In one embodiment, the fluid is selected from a group consisting of genes, growth factors, drugs, nutrients, and combination thereof for treating the sclera. In another embodiment, the stent delivery apparatus further comprises a second fluid exiting port being in fluid communication with Schlemm's canal, wherein the fluid is selected from a group consisting of genes, growth factors, drugs, anti-glaucoma drug, anti-inflammatory drugs, vasodilating drugs, nutrients, and combination thereof for treating the sclera.

Figure 11:
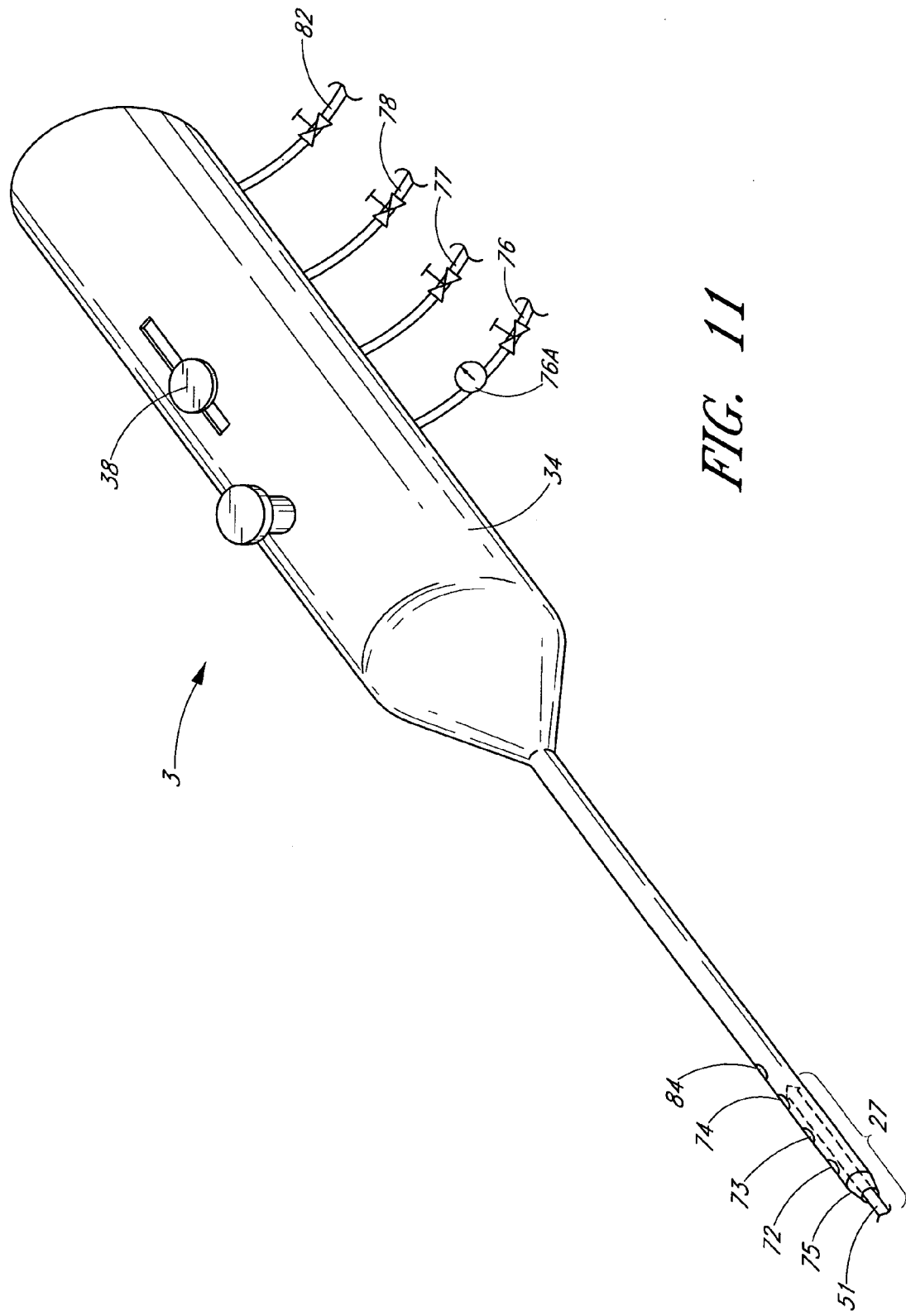
FIG. 11 shows one embodiment of an ab externo stent delivery applicator.

FIG. 11 shows one embodiment of an ab externo stent delivery applicator 3. The applicator 3 comprises a distal section 27 with a self-trephining type sharp cut end 75 and a handle section 34. A stent 51 is loaded within the distal section 27 with a sharp end 52 facing the operator. The applicator further comprises a plurality of fluid ports 72, 73, 74, 84 for administering various fluids to various target tissue sites. The multiple fluid channels and ports can be configured in the applicator according to ways that are well known to those of skill in the art, especially as seen in cardiovascular catheters. Each fluid supply source (76, 77, 78, 82) provides an appropriate fluid through a fluid channel (87, 86, 85, 83) to the fluid port (72, 73, 74, 84), respectively. All fluid channels 83, 85, 86, 87 are suitably placed within a lumen 9 of the stent delivery applicator 3 for providing a fluid to each fluid port. An appropriate fluid with at least one active component can be selected from a of gene, growth factor, drug, anti-glaucoma drug, vasodilating agent, saline, viscoelastic, anti-inflammatory drug, and/or the like.

Figure 12:
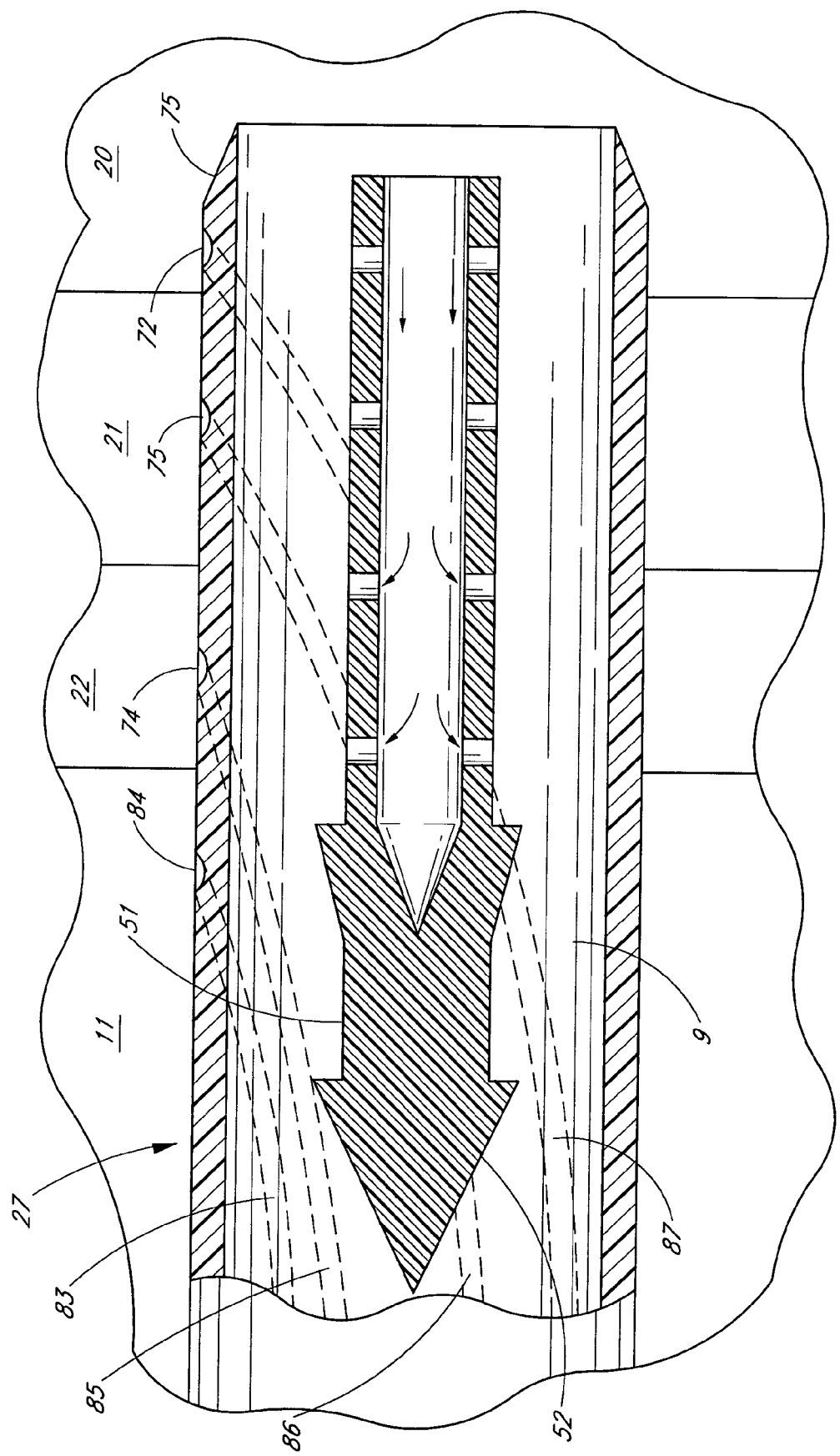
FIG. 12 shows a distal section of the ab externo stent delivery applicator of FIG. 11.

FIG. 12 shows a distal section 27 of the ab externo stent delivery applicator 3 of FIG. 11. A pressure monitor 76A is installed at a suitable place adjacent to the fluid supplier source 76, wherein the pressure monitor 76A is sized and configured to monitor the sensing pressure at about the first fluid port 72. In operations, the applicator 3 is inserted through a small opening at the sclera 11 and advanced toward Schlemm's canal using an external visualization aid that is known to one skilled in the art. During the course of the stent delivery phase ab externo, the sensing pressure at the first fluid port 72 reflects the pressures of the sclera 11, Schlemm's canal 22, the trabecular meshwork 21, and the anterior chamber 20 in sequence. In one embodiment, when the sensing pressure continuously increases until reach a plateau at the anterior chamber, it is indicative that the stent is ready to be unloaded from the applicator 3. Appropriate fluids can be administered to any or all of the following: the sclera 11 through the fluid port 84, Schlemm's canal through the fluid port 74, the trabecular meshwork through the fluid port 73, or the anterior chamber 20 through the fluid port 72. At the end of the stent delivery phase, the stent 51 can be unloaded from the applicator 3 by operating a knob 38 on the handle 34.

From the foregoing description, it should be appreciated that a novel approach for the surgical treatment of glaucoma has been disclosed for reducing intraocular pressure. While the invention has been described with reference to specific embodiments, the description is illustrative of the invention and is not to be construed as limiting the invention. Various modifications and applications may occur to those who are skilled in the art, without departing from the true spirit and scope of the invention, as described by the appended claims and their equivalents.

What is claimed is:

1. An implant for treating an ocular disorder, said implant having a longitudinal implant axis and comprising:
   an outflow portion through which said longitudinal implant axis passes, said outflow portion shaped and sized to be:
      (a) introduced into Schlemm's canal of an eye with said portion of said longitudinal implant axis at an angle to Schlemm's canal; and
      (b) received at least partially within Schlemm's canal regardless of a rotational orientation of the outflow portion about said longitudinal implant axis during said introduction;
   a plurality of longitudinally spaced openings in the outflow portion, the openings allowing fluid to communicate from a lumen within the outflow portion to a location outside the outflow portion;
   an inflow portion configured to be positioned within an anterior chamber of the eye so as to permit communication of fluid from the anterior chamber to the outflow portion; and
   an anchoring member extending from the implant and being disposed distally of the longitudinally spaced openings;
   wherein said longitudinal implant axis extends through a trabecular meshwork of the eye and is generally orthogonal to Schlemm's canal during said fluid communication.

2. The implant of claim 1, wherein the outflow portion has a distal end with a transverse dimension that varies along the longitudinal implant axis.

3. The implant of claim 2, wherein the distal end of the outflow portion has a generally conical shape.

4. The implant of claim 2, wherein the distal end of the outflow portion has at least one sloped surface.

5. The implant of claim 2, wherein the distal end and the outflow portion are integrally formed.

6. The implant of claim 1, wherein the anchoring member comprises a surface that is generally transverse to the longitudinal implant axis.

7. The implant of claim 1, further comprising an intermediate section between the inflow portion and the outflow portion.

8. The implant of claim 1, wherein at least a portion of the implant is configured to reside within the trabecular meshwork of the eye.

9. The implant of claim 1, wherein the outflow portion is shaped and sized to be introduced through Schlemm's canal of the eye.

10. The implant of claim 1, wherein the implant comprises a therapeutic drug.

11. The implant of claim 10, wherein the implant comprises a polymer.

12. The implant of claim 10, wherein the implant includes a first portion and a second portion that is appended from the first portion, and wherein the first portion includes the lumen and the second portion carries the therapeutic drug.

13. The implant of claim 10, wherein at least a portion of the implant is coated with the therapeutic drug.

14. The implant of claim 10, wherein the implant comprises a biocompatible material with the therapeutic drug coated thereon.

* * * * *

UNITED STATES PATENT AND TRADEMARK OFFICE
CERTIFICATE OF CORRECTION

PATENT NO.       : 7,488,303 B1                                              Page 1 of 1
APPLICATION NO.  : 10/667580
DATED            : February 10, 2009
INVENTOR(S)      : David S. Haffner et al.

It is certified that error appears in the above-identified patent and that said Letters Patent is hereby corrected as shown below:

Title Page; item (56); At column 1, line 10, Under Other Publications, please delete "Tanatlum" and insert therefore, --Tantalum--.

Title Page; item (56); At column 1, line 11, Under Other Publications, please delete "Opthalmology" and insert therefore, --Ophthalmology--.

Title Page; item (56); Page 3; At column 1, line 23, Under Foreign Patent Documents, please delete "6/1992" and insert therefore, --6/1994--.

Title Page; item (56); Page 3; At column 1, line 28, Under Foreign Patent Documents, please delete "EO" and insert therefore, --WO--.

Title Page; item (56); Page 3; At column 1, line 28, Under Foreign Patent Documents, please delete "2/1998" and insert therefore, --2/1989--.

Title Page; item (56); Page 3; At column 1, line 51, Under Other Publications, please delete "augenarztilchen" and insert therefore, --augenarztilcher--.

Title Page; item (56); Page 3; At column 1, line 51, Under Other Publications, please delete "XXXIII," and insert therefore, --XXXII.--.

Title Page; item (56); Page 3; At column 2, line 1, Under Other Publications, please delete "Arthue" and insert therefore, --Arthur--.

Signed and Sealed this

Twenty-ninth Day of September, 2009

David J. Kappos
*Director of the United States Patent and Trademark Office*